(12) United States Patent
Kodera et al.

(10) Patent No.: US 7,947,315 B2
(45) Date of Patent: May 24, 2011

(54) DAIRY PRODUCTS AND METHOD OF MANUFACTURING THE SAME

(75) Inventors: Tomohiro Kodera, Kawasaki (JP); Hiroyuki Nakagoshi, Kawasaki (JP); Noriko Miwa, Kawasaki (JP); Nami Nakamura, Kawasaki (JP); Hidehiko Wakabayashi, Kawasaki (JP)

(73) Assignees: Amano Enzyme Inc., Nagoya-shi (JP); Ajinomoto Co., Inc., Tokyo (JP)

( * ) Notice: Subject to any disclaimer, the term of this patent is extended or adjusted under 35 U.S.C. 154(b) by 359 days.

(21) Appl. No.: 11/777,601

(22) Filed: Jul. 13, 2007

(65) Prior Publication Data

US 2007/0254065 A1    Nov. 1, 2007

Related U.S. Application Data

(63) Continuation of application No. PCT/JP2006/300574, filed on Jan. 11, 2006.

(30) Foreign Application Priority Data

Jan. 13, 2005   (JP) .................................. 2005-005854

(51) Int. Cl.
*A23C 9/12* (2006.01)
(52) U.S. Cl. ................ 426/36; 426/34; 426/40; 426/42; 426/582; 426/583
(58) Field of Classification Search .................. 426/34, 426/36, 40, 42, 580, 582, 583
See application file for complete search history.

(56) References Cited

U.S. PATENT DOCUMENTS

| | | | | |
|---|---|---|---|---|
| 3,857,967 | A | * 12/1974 | Kikuchi et al. | ................. 426/18 |
| 5,681,598 | A | 10/1997 | Kuraishi et al. | |
| 6,756,221 | B1 | 6/2004 | Yamaguchi | |
| 7,008,653 | B2 | * 3/2006 | Matsumura et al. | ............ 426/42 |
| 2004/0072318 | A1 | 4/2004 | Yamaguchi et al. | |
| 2004/0166558 | A1 | 8/2004 | Yamaguchi et al. | |
| 2004/0175799 | A1 | 9/2004 | Yamaguchi | |

FOREIGN PATENT DOCUMENTS

| | | |
|---|---|---|
| JP | 6-197688 | 7/1994 |
| JP | 8-173032 | 7/1996 |
| JP | 11-042086 | 2/1999 |
| JP | 2000-014317 | 1/2000 |
| JP | 2000-50887 | 2/2000 |
| JP | 2001-120179 | 5/2001 |
| JP | 2001-218590 | 8/2001 |
| JP | 2003-250460 | 9/2003 |

OTHER PUBLICATIONS

U.S. Appl. No. 11/777,554, filed Jul. 13, 2007, Miwa, et al.
U.S. Appl. No. 11/777,601, filed Jul. 13, 2007, Kodera, et al.
U.S. Appl. No. 12/970,049, filed Dec. 16, 2010, Miwa, et al.
U.S. Appl. No. 11/777,601, filed Jul. 13, 2007, U.S. Patent App. Publication No. US2007/0254065 A1, Kodera, et al.

* cited by examiner

*Primary Examiner* — Leslie Wong
(74) *Attorney, Agent, or Firm* — Oblon, Spivak, McClelland, Maier & Neustadt, L.L.P.

(57) ABSTRACT

The present invention provides a dairy product with smooth oral sensation and suppressed acidic taste and bitter taste and a method for manufacturing the same, wherein a protein deamidating enzyme is added to raw milk to act on the milk protein in the raw milk.

17 Claims, No Drawings

SEQUENCE LISTING

<160> NUMBER OF SEQ ID NOS: 14

<210> SEQ ID NO 1
<211> LENGTH: 963
<212> TYPE: DNA
<213> ORGANISM: Chyrseobacterium proteolyticum
<220> FEATURE:
<221> NAME/KEY: misc_feature
<223> OTHER INFORMATION: protein glutaminase; nucleotide sequence

<400> SEQUENCE: 1

```
atgaagaacc ttttcctgtc catgatggcc ttcgtgaccg tcctcacctt caactcctgc      60
gccgattcca acggcaacca ggaaatcaac ggcaaggaga agctttccgt taacgattct     120
aagctgaagg atttcggcaa gaccgttccg gttggcatcg acgaagagaa cggcatgatc     180
aaggtgtcct tcatgttgac tgcgcagttc tacgagatca agccaaccaa ggaaaacgag     240
cagtacatcg gtatgcttcg ccaggctgtt aagaacgaat ctccagtcca cattttcctc     300
aagccaaaca gcaatgaaat cggcaaggtg gagtctgcat ccccagagga cgtccgctac     360
ttcaagacga tcctgaccaa agaagtcaag ggccagacca acaaattggc gtccgtcatt     420
ccagatgtgg ctaccctcaa ctctctcttc aaccaaatca agaaccagtc ttgcggtacc     480
tctacggcgt cctccccatg catcaccttc cgctacccag tcgacggctg ctacgcacgc     540
gcccacaaga tgcgccagat cttgatgaac aacggctatg actgtgagaa gcaattcgtg     600
tacggtaacc tcaaggcatc caccggcacc tgctgcgtgg cgtggagcta ccacgttgca     660
```

```
atcttggtga gctacaaaaa cgcttccggc gtgacggaaa aacgcattat tgatccatcc    720
cttttttcca gcggtcctgt gaccgatacc gcatggcgca acgcttgcgt taacacctct    780
tgcggctctg catccgtttc ctcttacgct aacaccgcag gaaatgttta ttaccgctcc    840
ccatccaatt cttacctgta tgacaacaat ctgatcaata ccaactgtgt cctgactaaa    900
ttctccctgc tttccggctg ttctccttca cctgcaccgg atgtctccag ctgtggattt    960
taa                                                                  963
```

<210> SEQ ID NO 2
<211> LENGTH: 320
<212> TYPE: PRT
<213> ORGANISM: Chyrseobacterium roteollyticum
<220> FEATURE:
<221> NAME/KEY: MISC_FEATURE
<223> OTHER INFORMATION: protein glutaminase; amino acid sequence

<400> SEQUENCE: 2

```
Met Lys Asn Leu Phe Leu Ser Met Met Ala Phe Val Thr Val Leu Thr
1               5                   10                  15

Phe Asn Ser Cys Ala Asp Ser Asn Gly Asn Gln Glu Ile Asn Gly Lys
            20                  25                  30

Glu Lys Leu Ser Val Asn Asp Ser Lys Leu Lys Asp Phe Gly Lys Thr
        35                  40                  45

Val Pro Val Gly Ile Asp Glu Glu Asn Gly Met Ile Lys Val Ser Phe
    50                  55                  60

Met Leu Thr Ala Gln Phe Tyr Glu Ile Lys Pro Thr Lys Glu Asn Glu
65                  70                  75                  80

Gln Tyr Ile Gly Met Leu Arg Gln Ala Val Lys Asn Glu Ser Pro Val
                85                  90                  95

His Ile Phe Leu Lys Pro Asn Ser Asn Glu Ile Gly Lys Val Glu Ser
            100                 105                 110

Ala Ser Pro Glu Asp Val Arg Tyr Phe Lys Thr Ile Leu Thr Lys Glu
        115                 120                 125

Val Lys Gly Gln Thr Asn Lys Leu Ala Ser Val Ile Pro Asp Val Ala
    130                 135                 140

Thr Leu Asn Ser Leu Phe Asn Gln Ile Lys Asn Gln Ser Cys Gly Thr
145                 150                 155                 160

Ser Thr Ala Ser Ser Pro Cys Ile Thr Phe Arg Tyr Pro Val Asp Gly
                165                 170                 175

Cys Tyr Ala Arg Ala His Lys Met Arg Gln Ile Leu Met Asn Asn Gly
            180                 185                 190

Tyr Asp Cys Glu Lys Gln Phe Val Tyr Gly Asn Leu Lys Ala Ser Thr
        195                 200                 205

Gly Thr Cys Cys Val Ala Trp Ser Tyr His Val Ala Ile Leu Val Ser
    210                 215                 220

Tyr Lys Asn Ala Ser Gly Val Thr Glu Lys Arg Ile Ile Asp Pro Ser
225                 230                 235                 240

Leu Phe Ser Ser Gly Pro Val Thr Asp Thr Ala Trp Arg Asn Ala Cys
                245                 250                 255

Val Asn Thr Ser Cys Gly Ser Ala Ser Val Ser Ser Tyr Ala Asn Thr
            260                 265                 270

Ala Gly Asn Val Tyr Tyr Arg Ser Pro Ser Asn Ser Tyr Leu Tyr Asp
        275                 280                 285

Asn Asn Leu Ile Asn Thr Asn Cys Val Leu Thr Lys Phe Ser Leu Leu
    290                 295                 300
```

```
Ser Gly Cys Ser Pro Ser Pro Ala Pro Asp Val Ser Ser Cys Gly Phe
305                 310                 315                 320
```

<210> SEQ ID NO 3
<211> LENGTH: 117
<212> TYPE: DNA
<213> ORGANISM: Escherichia coli
<220> FEATURE:
<221> NAME/KEY: misc_feature
<223> OTHER INFORMATION: TorA signal sequence; nucleotide sequence

<400> SEQUENCE: 3

```
atgaacaata acgatctctt tcaggcatca cgtcggcgtt ttctggcaca actcggcggc      60
ttaaccgtcg ccgggatgct ggggccgtca ttgttaacgc cgcgacgtgc gactgcg       117
```

<210> SEQ ID NO 4
<211> LENGTH: 39
<212> TYPE: PRT
<213> ORGANISM: Escherichia coli
<220> FEATURE:
<221> NAME/KEY: MISC_FEATURE
<223> OTHER INFORMATION: TorA signal peptide

<400> SEQUENCE: 4

```
Met Asn Asn Asn Asp Leu Phe Gln Ala Ser Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
        35
```

<210> SEQ ID NO 5
<211> LENGTH: 21
<212> TYPE: DNA
<213> ORGANISM: Artificial Sequence
<220> FEATURE:
<223> OTHER INFORMATION: synthetic olygonucleotide

<400> SEQUENCE: 5

```
catgaagaac cttttcctgt c                                               21
```

<210> SEQ ID NO 6
<211> LENGTH: 26
<212> TYPE: DNA
<213> ORGANISM: Artificial Sequence
<220> FEATURE:
<223> OTHER INFORMATION: synthetic olygonucleotide

<400> SEQUENCE: 6

```
gtaaaaggat ccattaatta aaatcc                                          26
```

<210> SEQ ID NO 7
<211> LENGTH: 25
<212> TYPE: DNA
<213> ORGANISM: Artificial Sequence
<220> FEATURE:
<223> OTHER INFORMATION: synthetic olygonucleotide

<400> SEQUENCE: 7

```
atgaacaata acgatctctt tcagg                                           25
```

<210> SEQ ID NO 8
<211> LENGTH: 26
<212> TYPE: DNA
<213> ORGANISM: Artificial Sequence
<220> FEATURE:

<223> OTHER INFORMATION: synthetic olygonucleotide

<400> SEQUENCE: 8
ccggatcctg gtcatgattt cacctg                                    26

<210> SEQ ID NO 9
<211> LENGTH: 26
<212> TYPE: DNA
<213> ORGANISM: Artificial Sequence
<220> FEATURE:
<223> OTHER INFORMATION: synthetic olygonucleotide

<400> SEQUENCE: 9
aaattcctgt gaattagctg atttag                                    26

<210> SEQ ID NO 10
<211> LENGTH: 43
<212> TYPE: DNA
<213> ORGANISM: Artificial Sequence
<220> FEATURE:
<223> OTHER INFORMATION: synthetic olygonucleotide

<400> SEQUENCE: 10
aagagatcgt tattgttcat agaggcgaag gctcccttgaa tag                 43

<210> SEQ ID NO 11
<211> LENGTH: 44
<212> TYPE: DNA
<213> ORGANISM: Artificial Sequence
<220> FEATURE:
<223> OTHER INFORMATION: synthetic olygonucleotide

<400> SEQUENCE: 11
gatttcctgg ttgccgttgg aatccgcagt cgcacgtcgc ggcg                 44

<210> SEQ ID NO 12
<211> LENGTH: 20
<212> TYPE: DNA
<213> ORGANISM: Artificial Sequence
<220> FEATURE:
<223> OTHER INFORMATION: synthetic olygonucleotide

<400> SEQUENCE: 12
gattccaacg gcaaccagga                                           20

<210> SEQ ID NO 13
<211> LENGTH: 33
<212> TYPE: DNA
<213> ORGANISM: Artificial Sequence
<220> FEATURE:
<223> OTHER INFORMATION: synthetic olygonucleotide

<400> SEQUENCE: 13
cttggggccg aagcccttga cttctttggt cag                            33

<210> SEQ ID NO 14
<211> LENGTH: 33
<212> TYPE: DNA
<213> ORGANISM: Artificial Sequence
<220> FEATURE:
<223> OTHER INFORMATION: synthetic olygonucleotide

<400> SEQUENCE: 14
ttcggcccca agttggcgtc cgtcattcca gat                            33

DAIRY PRODUCTS AND METHOD OF MANUFACTURING THE SAME

CROSS-REFERENCE TO RELATED APPLICATIONS

The present application is a continuation of PCT/JP06/300574, filed on Jan. 11, 2006, which claims priority to Japanese Application No. JP 2005-005854, filed on Jan. 13, 2005, which are hereby incorporated by reference in their entirety.

BACKGROUND OF THE INVENTION

1. Field of the Invention

The present invention relates to dairy products that are manufactured by using a protein deamidating enzyme and present smooth oral sensation with suppressed acidic taste and bitter taste. The present invention also provides a method of manufacturing the foregoing.

2. Discussion of the Background

Dairy products such as cheese, yogurt, etc. were once unfamiliar foodstuffs for Japanese. However, in recent years, their consumption has increased due to their health and nutrition-related functions. Thus, a variety of dairy products are on the market to meet diversified food preference of consumers.

Rennet is a milk-clotting enzyme for cheese, which is well-known in the filed for manufacturing dairy products. Further, a method utilizing a transglutaminase for cheese (Japanese Patent Application Laid-Open (Kokai) No. Hei 8-173032) and a method utilizing the same for yogurt (Japanese Patent Application Laid-Open (Kokai) No. Hei 6-197688) are also known.

Japanese Patent Application Laid-Open (Kokai) No. 2000-50887 discloses a method for using a protein deamidating enzyme to deamidate casein, thereby to improve the dispersibility and solubility thereof, and a method of manufacturing pudding-like foods which comprises allowing a transglutaminase to act on concentrated milk, wherein a protein deamidating enzyme is added to terminate the transglutaminase action. Japanese Patent Application Laid-Open (Kokai) No. 2001-218590 discloses a method wherein a protein deamidating enzyme is allowed to act on a milk caseinate or a whey protein, in order to deamidate, thereby to improve the foaming properties, emulsification, and solubility thereof. Japanese Patent Application Laid-Open (Kokai) No. 2003-250460 discloses a method wherein a protein deamidating enzyme is allowed to act on β-lactoglobulin, in order to deamidate, thereby to improve the properties in foaming and emulsification.

However, these patent documents do not describe a method for providing a dairy product according to the present invention which presents smooth oral sensation with suppressed acidic taste and bitter taste. In particular, none of the foregoing references disclose a cheese and/or yogurt which present smooth oral sensation with suppressed acidic taste and bitter taste. As such, there remains a critical need for a method of producing a dairy product according to the present invention which presents smooth oral sensation with suppressed acidic taste and bitter taste, as well as a dairy product produced thereby.

SUMMARY OF THE INVENTION

It is an object of the present invention to provide a dairy product which presents smooth oral sensation with suppressed acidic taste.

It is also an object of the present invention to provide a method for manufacturing a dairy product which presents smooth oral sensation with suppressed acidic taste, in order to meet diversified preference in taste of consumers.

The present inventors have made an intensive and extensive study to solve the above-mentioned objects, and found that a protein deamidating enzyme can be added to raw milk to act on the milk protein in the raw milk. As such, the present invention is exemplified by the following embodiments:

(1.) A method for manufacturing a dairy product comprising adding a protein deamidating enzyme to raw milk and maintaining said protein deamidating enzyme in contact with said milk protein in the raw milk for a time and under conditions suitable to permit the enzyme to deamidate said milk protein.

(2.) The method according to (1), wherein said protein deamidating enzyme is prepared from culture liquid of a microorganism producing said protein deamidating enzyme.

(3.) The method according to (1), wherein said protein deamidating enzyme is powderized prior to said adding.

(4.) The method according to (1), wherein the activity of said protein deamidating enzyme is confirmed prior to said adding by a method comprising:

(a) An aqueous solution (10 µl) containing a protein deamidating enzyme is added to 100 µl of 176 mM phosphate buffer (pH 6.5) containing 30 mM of Z-Gln-Gly, incubated at 37° C. for 10 minutes and the reaction is stopped by an addition of 12% TCA solution;

(b) The enzyme concentration is adjusted to 0.05 mg/ml by an appropriate dilution with using 20 mM phosphate buffer (pH 6.0) and, after a centrifugal separation, the supernatant liquid is subjected to quantitative measurement of $NH_3$;

(c) 10 µl of the supernatant liquid and 190 µl of 0.1 M triethanolamine buffer (pH 8.0) are added to 100 µl of a reagent II liquid, the mixture is allowed to stand at room temperature for 5 minutes and the absorbance at 340 nm is measured;

(d) Measurement of the concentration of protein is carried out at a detection wavelength of 595 nm using a protein assay CBB (Coomassie Brilliant Blue) solution; and (e) The activity of a protein deamidating enzyme is determined by the following expression:

Specific Activity (U/mg)=[(Ammonia concentration (µmol/ml) in reaction solution)×(Amount (ml) of reaction solution)×(Diluted rate of enzyme)]/ [(Amount (ml) of enzyme solution)×(Concentration (mg/ml) of protein)×(Reaction time (min))].

(5.) The method according to (1), wherein said raw milk is an edible milk selected from the group consisting of cow milk, buffalo milk, goat milk, sheep milk, and horse milk.

(6.) The method according to (1), wherein said raw milk is in a form selected from the group consisting of a pasteurized milk, a milk formulated in milk fat, a diluted milk, a concentrated milk, a dried milk, a defatted dry milk, a defatted milk solution, and a processed milk.

(7.) The method according to (1), wherein said dairy product is a solid food.

(8.) The method according to (1), wherein said dairy product is a gel food.

(9.) The method according to (1), wherein said dairy product is a solid food or a gel food produced from a raw material selected from the group consisting of a natural cheese, a processed cheese, a set yogurt, a stirred yogurt, a bavarois, a milk jelly, and a pudding.

(10.) The method according to (1), wherein said dairy product is cheese or yogurt.

(11.) The method according to (1), wherein said protein deamidating enzyme is added in an amount ranging from 0.1 to 500 units per 1 L of said raw milk.

(12.) The method according to (1), wherein said protein deamidating enzyme is added in an amount ranging from 0.1 to 100 units per 1 L of said raw milk.

(13.) The method according to (1), wherein the temperature during said maintaining ranges from 5 to 80° C.

(14.) The method according to (1), wherein the temperature during said maintaining ranges from 20 to 60° C.

(15.) The method according to (1), wherein the pH during said maintaining ranges from 2 to 10.

(16.) The method according to (1), wherein the pH during said maintaining ranges from 4 to 8.

(17.) The method according to (1), wherein said maintaining is for a time ranging from 10 seconds to 48 hours.

(18.) The method according to (1), wherein said maintaining is for a time ranging from 10 minutes to 24 hours.

(19.) The method according to (1), wherein said protein deamidating enzyme is encoded by a polynucleotide having the sequence of SEQ ID NO: 1.

(20.) The method according to (1), wherein said protein deamidating enzyme has the amino acid sequence of SEQ ID NO: 2.

(21.) The method according to (1), wherein said protein deamidating enzyme corresponds to the mature peptide fragment of the amino acid sequence of SEQ ID NO: 2.

(22.) A dairy product produced by the method of (1).

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the food sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The protein deamidating enzyme according to the present invention acts directly on the amide groups of a protein and has an activity to deamidate with neither peptide bond cleavage nor protein crosslink accompanied. The protein deamidating enzyme is not particularly limited in type so far as it has the action. An enzyme disclosed in Japanese Patent Application Laid-Open (Kokai) No. 2000-50887 or Japanese Patent Application Laid-Open (Kokai) No. 2001-21850 is an example of such enzymes, but the enzymes of the present invention are not limited to them. A protein deamidating enzyme may be used, which has been prepared from the culture broth of a microorganism producing the protein deamidating enzyme. Microorganisms to be used for preparation of the protein deamidating enzyme are not particularly limited.

In order to prepare the protein deamidating enzyme from the culture broth of a microorganism, any known method for protein separation and protein purification (centrifugation, UF concentration, salting-out, and various chromatographies using ion exchange resin or the like) may be used. For example, a culture broth can be centrifuged to remove the microorganism cells, followed by salting out, chromatography and the like in combination to obtain the target enzyme.

In order to collect the intracellular enzyme from microbial cells, for example, the microbial cells are first subjected to pressurization, ultrasonic treatment or the like to crush, and the target enzyme is then separated and purified as described above. In this connection, a microorganism culture broth may be in advance subjected to filtration or centrifugation to collect the microorganism cells, which are subjected to a series of the above-mentioned steps (disrupt of the microbial cells, separation, purification of the enzyme). The enzyme may be powdered by drying step such as freeze drying, reduced-pressure drying, or the like, during which appropriate bulking agent(s) or drying aid(s) may be used.

Activity of a protein deamidating enzyme of the present invention is determined by a modified method of the method described in Japanese Patent Application Laid-Open (Kokai) No. 2000-50887. Specifically, the following method may be employed:

(1) 10 µl of an aqueous solution containing the protein deamidating enzyme is added to 100 µl of 176 mM phosphate buffer (pH 6.5) containing 30 mM Z-Gln-Gly, and the reaction mixture is incubated at 37° C. for 10 min, followed by adding 100 µl of 12% TCA solution thereto, whereby the reaction is terminated.

(2) The resultant solution is diluted appropriately with 20 mM phosphate buffer (pH 6.0) to adjust an enzyme concentration to 0.05 mg/ml, and centrifuged (12000 rpm, 4° C., 5 min) to obtain a supernatant, which is analyzed to quantify $NH_3$ by an F-kit ammonia (manufactured by Roche).

(3) 10 µl of the supernatant and 190 µl of 0.1 M triethanolamine buffer (pH 8.0) are added to 100 µl of the reagent II solution (F-kit accessory), and left to stand at room temperature for 5 min. 100 µl of the resulting solution is used to determine the absorbance at 340 nm. The remaining 200 µl of the resulting solution is added with 1.0 µl of the reagent III (F-kit accessory, glutamate dehydrogenase), left to stand at room temperature for further 20 min, and then is used to determine the absorbance at 340 nm. The ammonia standard solution attached to the F-kit is used to make a calibration curve showing a relation between ammonia concentration and change in absorbance (340 nm), and the curve is used to determine the concentration of ammonia in the reaction solution.

(4) The protein assay CBB (Coomassie Brilliant Blue) solution (manufactured by Nacalai Tesque) is used to determine a protein concentration at a detection wavelength of 595 nm. BSA (manufactured by Pierce) is used as the standard.

(5) The activity of the protein deamidating enzyme is determined by the following equation:

Specific activity (U/mg)=(Concentration of ammonia in reaction solution (µmol/ml)×Reaction solution volume (ml)×Enzyme dilution rate)÷(Volume of enzyme solution (ml)×Protein concentration (mg/ml)×Reaction time (min))

As used in the present specification, an enzyme activity that releases 1 µmol of ammonia per 1 minute is defined as 1 unit (U).

The raw milk to be used according to the present invention is an edible milk such as cow milk, buffalo milk, goat milk, sheep milk, horse milk and the like. Further, for each of the foregoing, a pasteurized milk, a milk formulated in component such as milk fat, a diluted milk, a concentrated milk, a dried milk, a defatted dry milk, a defatted milk solution, and a processed milk are included in this category.

The dairy product of the present invention includes a solid or gel food produced using, as the raw material, a natural cheese, a processed cheese, a set yogurt, a stirred yogurt, a bavarois, a milk jelly, a pudding and the like.

The protein deamidating enzyme may be added to raw milk, alone or in combination with other raw material(s). The reaction conditions for the protein deamidating enzyme (such as enzyme amount, reaction time, temperature, pH of the reaction solution and the like) are not particularly limited, but the enzyme is added preferably in an amount of 0.1 to 500 units, more preferably 0.1 to 100 units per 1 L of the raw milk.

In the case of a processed milk such as diluted milk, concentrated milk, dried milk, defatted dry milk or the like, the protein deamidating enzyme is used in an amount based on the volume in terms of a volume of the raw milk before processed. For example, when 100 g of defatted dry milk is obtained from 1 L of the raw milk, 0.1 to 500 units of the enzyme per 100 g of the defatted dry milk that corresponds to 1 L of the raw milk are preferable and 0.1 to 100 units are more preferable.

The reaction temperature is preferably 5-80° C., more preferably 20-60° C.

The pH of the reaction solution is preferably 2-10, more preferably 4-8.

The reaction time is preferably 10 sec to 48 hours, more preferably from 10 min to 24 hours.

The foregoing conditions may be changed or adjusted appropriately depending on purity of the enzyme to use, kind and purity of protein to use, or the like. The solution after enzyme reaction may be, for example, heated to deactivate the enzyme in order to manufacture a dairy product, or may be subjected to no special deactivation in the same way as a rennet is.

The dairy product such as defatted dry milk or the like, which is improved in quality by adding raw milk with a protein deamidating enzyme to deamidate, may be added at a step for manufacturing other dairy products such as cheese, yogurt and the like. For example, a modified defatted dry milk, which is produced by adding 100 g of a defatted dry milk with 0.1 to 500 units, preferably 20 to 100 units of the enzyme, can be added to raw milk at a rate of 1-5% to manufacture a yogurt which smoothness is imparted to.

In accordance with the present invention, it is possible to provide a diary product with smooth oral sensation and suppressed acidic taste and bitter taste, and to manufacture cheese at improved curd yields. Therefore, the present invention is extremely useful in the industrial field of foods.

The above written description of the invention provides a manner and process of making and using it such that any person skilled in this art is enabled to make and use the same, this enablement being provided in particular for the subject matter of the appended claims, which make up a part of the original description. Preferred embodiments of the invention are similarly fully described and enabled.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

A protein glutaminase derived from Chryseobacterium was used as the protein deamidating enzyme. The gene sequence of the protein glutaminase (EC.3.5.1) derived from *Chryseobacterium proteolyticum* strain has already been determined [Eur. J, Biochem. 268, 1410-1421 (2001)]. In view of the sequence, a gene sequence represented by SEQ ID NO: 1 was constructed following codon optimization, wherein the native codons were converted to the corresponding frequently used codon in *Corynebacterium glutamicum*. This sequence includes a signal sequence (pre-portion) and a pro-portion of the protein glutaminase, and a region for coding the mature protein glutaminase. The whole gene sequence was produced by synthesis.

Based on the gene sequence represented of SEQ ID NO: 1, primers having sequences represented by SEQ ID NO: 5 (5'-CATGAAGAACCTTTTCCTGTC-3') and SEQ ID NO: 6 (5'-GTAAAAGGATCCATTAATTAAAATCC-3') were synthesized. The primer of SEQ ID NO: 5 included the N-terminal sequence of the signal sequence of the protein glutaminase, and the primer of SEQ ID NO: 6 included the C-terminal sequence of the mature protein glutaminase and the recognition sequence for BamHI. The DNA of SEQ ID NO: 1 was used as the PCR template, and the primers having the sequences of SEQ ID NO: 5 and SEQ ID NO: 6 were used to perform PCR, thereby to amplify the regions coding for the pro-portion of the protein glutaminase and the mature protein glutaminase.

The resulting PCR fragment was inserted into SmaI site of pVC7 described in Japanese Patent Application Laid-Open (Kokai) No. Hei 9-070291 to produce a plasmid. Competent *E. coli* JM109 cells (manufactured by Takara Shuzo) were then transduced with the plasmid to produce a strain carrying the plasmid with the cloned protein glutaminase gene therein. The plasmid was then collected from *E. Coli* JM109. The nucleic acid sequence of the fragment cloned in this plasmid was determined to confirm that it coincided with the sequence of SEQ ID NO: 1.

The sequence of TorA gene including TorA signal peptide derived from *E. coli* has been previously described (Mol. Microbiol. 11:1169-1179 (1994)). Primers shown in SEQ ID NO: 7 (5'-ATGAACAATAACGATCTCTTTCAGG-3') and in SEQ ID NO: 8 (5'-CCGGATCCTGGTCATGATTTCACCTG-3') were synthesized based on the known sequence of the TorA gene. Chromosomal DNA of *E. coli* W3110 strain prepared according to standard protocols (Method by Saitoh and Miura [Biochim. Biophys. Acta, 72, 619 (1963)]) was used as the PCR template, thus amplifying the region for coding TorA and the region including the signal sequence located upstream. The PCR reaction was performed using Pyrobest DNA polymerase (manufactured by Takara Shuzo) under reaction conditions established according to the protocol recommended by the vendor. Notably, the sequence shown in SEQ ID NO: 8 included a recognition sequence for restriction enzyme BamHI.

The DNA sequence coding the signal sequence of TorA is shown in SEQ ID NO: 3. Plasmid pPKSPTG1 described in International Patent Publication WO 01/23591 was used as the template, and the primer having sequences shown in SEQ ID NO: 9 (5'-AAATTCCTGTGAATTAGCTGATTTAG-3') and SEQ ID NO: 10 (5'-AAGAGATCGTTATTGTTCATA-GAGGCGAAGGCTCCTTGAATAG-3') were used for PCR amplification of the regions for coding the promoter and the signal peptide. The sequence shown in SEQ ID NO: 10 includes the 5'-terminal sequence of the gene for coding the TorA signal peptide.

The PCR product was then mixed with the PCR product comprising a region containing a gene sequence for coding the TorA amplified by the primers having the sequences shown in SEQ ID NO: 7 and SEQ ID NO: 8 and a signal sequence located upstream thereof, at a ratio of 1:1 to give a mixture. This mixture was used as a template to perform cross-over PCR using the primers having the sequences of SEQ ID NO: 8 and SEQ ID NO: 9. Through these manipulations, a fusion gene comprising a sequence including a PS2 promoter region, a TorA signal sequence and a sequence coding for the TorA was amplified. This cross-over PCR product was digested by restriction enzymes ScaI and BamHI, and subjected to agarose gel electrophoresis to detect an approximately 3.1 kbp DNA fragment. The 3.1 kbp DNA fragment was separated from the agarose gel, collected by EasyTrapVer.2 (manufactured by Takara Shuzo), and inserted into the ScaI-BamHI site of the plasmid pPK4 described in Japanese Patent Application Laid-Open (Kokai) No. Hei 9-322774 resulting in a pPKT-TorA plasmid. Determination of the nucleic acid sequence of the gene sequence inserted into this plasmid confirmed that the expected fusion gene had been constructed.

This plasmid was used as the template, and primers having their respective sequences shown in SEQ ID NO: 9 and SEQ ID NO: 11 (5'-GATTTCCTGGTTGCCGTTGGAATCCG-CAGTCGCACGTCGCGGCG-3') were used to perform a PCR, thereby to amplify a portion including the promoter region of PS2 and the region for coding the TorA signal peptide. The sequence shown in SEQ ID NO: 11 has the 5'-terminal sequence of the region for coding a protein deamidating enzyme with a pro-sequence.

Next, a plasmid wherein a protein deamidating enzyme was cloned was used as the template, and primers having their respective sequences shown in SEQ ID NO: 6 and SEQ ID NO: 12 (5'-GATTCCAACGGCAACCAGGA-3') were used to PCR amplify the region coding for the protein glutaminase with a pro-sequence. Further, these PCR products were mixed at a ratio of 1:1 to give a mixture, which was used as the template, and primers having their respective sequences shown in SEQ ID NO: 6 and SEQ ID NO: 9 were used to perform a cross-over PCR to amplify a fusion gene of the gene for coding the PS2 promoter region and the gene for coding the TorA signal sequence and the protein glutaminase with a pro-sequence.

This PCR product was digested by restriction enzymes ScaI and BamHI, and subjected to agarose gel electrophoresis to detect an approximately 3.1 kbp DNA fragment. This DNA fragment was separated from the agarose gel, collected using EasyTrapVer.2 (manufactured by Takara Shuzo), and inserted into ScaI-BamHI site of the plasmid pPK4 described in the said Japanese Patent Application Laid-Open (Kokai) No. Hei 9-322774 to obtain a plasmid pPKT-PPG. Determination of the nucleic acid sequence of the inserted sequence in the plasmid confirmed that it was the expected fusion gene. The amino acid sequence of a protein glutaminase with a pro-sequence is shown in SEQ ID NO: 2 and the amino acid sequence of the TorA signal peptide is shown in SEQ ID NO: 4.

However, it was anticipated that the amino acid sequence of a natural type protein glutaminase would be maturated by a commercially available protease to give no correctly cleaved pro-sequence. Accordingly, "QTNK" in the C-terminal sequence of the pro-sequence was changed to "FGPK" so that the pro-sequence might be cleaved to get the same sequence as the N-terminal sequence of the natural type protein glutaminase. Primers having their respective sequences shown in SEQ ID NO: 13 (5'-CTT GGG GCC GAA GCC CTT GAC TTC TTT GGT CAG-3') and SEQ ID NO: 14 (5'-TTC GGC CCC AAG TTG GCG TCC GTC ATT CCA GAT-3') were used in order to change to "FGPK". The sequence shown in SEQ ID NO: 13 is a primer for amplifying the pro-sequence portion, and the sequence shown in SEQ ID NO: 14 is a primer for amplifying the matured form portion.

Using pPKT-PPG as the template, the primers having their respective sequences shown in SEQ ID NO: 12 and SEQ ID NO: 13 were used to amplify the pro-sequence portion of the protein glutaminase, and the primers having their respective sequences shown in SEQ ID NO: 14 and SEQ ID NO: 6 were used to amplify the matured form portion of the protein glutaminase. These PCR products were mixed at a ratio of 1:1 to give a mixture, which was used as the template, and the primer having their respective sequences shown in SEQ ID NO: 6 and SEQ ID NO: 12 were used to perform a cross-over PCR to amplify the protein glutaminase gene with a pro-sequence wherein the C-terminal of the pro-sequence was changed to FGPK. This cross-over PCR product was cloned into the SmaI site of pUC18 (pUCPPG (FGPK)) to confirm the nucleic acid sequence, indicating that the pro sequence had been changed. Next, an AatII-BstPI fragment (large) of pPKT-PPG and an AatII-BstPI fragment (small) of pUCPPG (FGPK) were ligated to construct pPKT-PPG (FGPK).

C. glutamicum ATCC13869 was transformed with the plasmid pPKT-PPG (FGPK), and incubated in CM2G agar culture medium containing 25 mg/l of kanamycin to select a transformant. The selected strain was incubated in the MM liquid culture containing 25 mg/l of kanamycin at 30° C. for 48 hours. The C. glutamicum culture broth was centrifuged to obtain a supernatant, which was then filtered off (0.45 μm). The filtered solution was condensed using an ultrafiltration membrane (to exclude those having a molecular weight of 10,000 Da or less). The buffer was exchanged with 50 mM phosphate buffer (pH 7.5), and the pro-sequence portion of the protein deamidating enzyme was cleaved by trypsin to allow maturation. Then, the resultant solution was concentrated again, and the buffer was exchanged (20 mM acetate buffer, pH 5.0). The concentrated sample obtained was subjected to cation exchange chromatography to purify the active fraction of the protein deamidating enzyme. The activity per protein of the purified enzyme was analyzed according to the previously described method, and it was around 100-140 U/mg.

Full-fat milk was homogenized (pre-heated at 60° C., 30 kgf/cm$^2$), pasteurized (72° C., 15 sec), and cooled to 31° C. to give a raw milk. 25 L of the raw milk was divided into caldrons to which a lactic acid bacterium starter (CHN-01: four-in-one mixture) (1% of the milk) was added along with 2, 10, and 50 units of the above-mentioned purified protein deamidating enzyme product (100 units/mg) per 1 L of the raw milk. Further, 0.01% CaCl$_2$, and 0.003% rennet were added to perform cutting (pH 6.2 on cutting). The resultant mass was added with hot water with light stirring, warmed (32° C.), left to stand, and the whey was removed when the pH lowered down to 5.8. Further, the resultant curd was subjected to matting (set temperature 34° C., up to pH 5.2) and molding (reversed twice or three times every 30 min), left to stand overnight at 20° C. (pH 5.2), and then cut into 125 g/piece. The pieces were salted (immersed in saturated NaCl solution for 3 min), dried (3 days at 5° C.), vacuum-packed, and matured at 13° C. The product was molded, left to stand overnight to give a curd, the weight of which was measured to calculate a curd yield. The fresh cheese left for one week was subjected to sensory test. Results obtained are shown in Table 1.

As shown in Table 1, treatment of raw milk with the protein deamidating enzyme improves a curd yield and allows production of cheese with smooth oral sensation and suppressed acidic taste.

TABLE 1

Curd Yield and Results of Sensory Test on Fresh Cheese

| Amount of enzyme added (Unit/milk 1 L) | Curd yield (%) | Smoothness of oral sensation | Acidic taste |
| --- | --- | --- | --- |
| 0 | 13.7 | ± | ± |
| 2 | 14.4 | ++ | -- |
| 10 | 14.8 | +++ | -- |
| 50 | 15.6 | +++ | -- |

±: Control,
+: Increase,
−: Decrease

Example 2

800 mL of commercially available low-temperature pasteurized milk was added to a jug, heated to 90° C. with stirring on a hot-water bath, and cooled down to 48° C. 80 ml of a started ("Danone" yogurt) was added to the jug and divided into every 100 ml, which was then added with the purified protein deamidating enzyme product (100 units/mg) prepared according to the method described in Example 1 by 1, 5, 10, 50, or 100 units per 1 L of the milk, stirred thoroughly, and divided into every approximately 20 mL in a container before it got cold. It was incubated in an incubator set to 48° C. for 3-4 hours, and found to have a yogurt pH of 4.4 to 4.5, upon which it was stored in a refrigerator to terminate fermentation. It was stored overnight at 4° C., and, on the following day, analyzed using a texture analyzer to perform property determination and sensory test. Results are shown in Table 2.

As shown in Table 2, the addition of protein deamidating enzyme to the raw milk allowed production of a yogurt with smooth oral sensation and suppressed acidic taste. Similarly, a method, wherein the protein deamidating enzyme acted on the raw milk at 50° C. for 90 min, and then heated at 90° C. for 5 min to be deactivated, followed by adding a starter and fermenting at 38° C. to have a pH of 4.5, provided a yogurt with smooth oral sensation, especially very smooth oral sensation felt at the end of its eating.

TABLE 2 pH and Results of Sensory Test of Yogurt

| Amount of enzyme added (Unit/milk 1 L) | pH | Rupture stress (g) | Smoothness of oral sensation | Acidic Taste |
| --- | --- | --- | --- | --- |
| 0 | 4.52 | 24.2 | ± | ± |
| 1 | 4.59 | 23.5 | + | − |
| 5 | 4.47 | 19.8 | ++ | -- |
| 10 | 4.45 | 16.8 | +++ | -- |
| 50 | 4.47 | 12.7 | ++++ | -- |
| 100 | 4.51 | Measurement impossible | +++++ | --- |
| 500 | 4.60 | Measurement impossible | +++++ | --- |

±: Control,
+: Increase,
−: Decrease

Example 3

40 g of defatted dry milk (low heat; manufactured by National Federation of Dairy Cooperative Associations) was suspended in 800 ml of distilled water. To the resultant suspension 0.2 or 1 unit of the purified protein deamidating enzyme product (100 units/mg) prepared according to the method described in Example 1 was added, per 1 g of the defatted dry milk (20 units or 100 units in terms of per 1 L of the raw milk), and subjected to reaction at 40° C. for 2.5 hours, followed by heating to deactivate (at 65° C. for 30 min; 1 hour for rising temperature). The deactivated mass was freeze-dried to prepare a modified defatted dry milk. Raw milk was added to the modified defatted dry milk at a rate of 1 to 5% of the raw milk, to prepare a yogurt according to the same method as in Example 2. The amount of 0.2 U/g was a condition for slightly deamidating the Gln in the defatted dry milk, and the amount of 1 U/g was a condition for deamidating approximately 50% of the Gln which was able to be deamidated. As a control, an unmodified defatted dry milk was used.

A sensory test was carried out for each of the samples and it was found that the enzyme-untreated defatted dry milk could be added to provide a yogurt with increased solid content, thereby to furnish it with improved oral sensation and high-quality sense, compared with a yogurt with no defatted dry milk added. Meanwhile, the defatted dry milk, which was treated with 0.2 U/g of the protein deamidating enzyme, could be added to produce a yogurt with smooth oral sensation that began at a rate of 1% of the raw milk and got remarkably effective at that of 3% or more. The defatted dry milk, which was treated with 1 U/g of the enzyme, could be added at a rate of 1% of the raw milk to produce a yogurt with remarkable smooth oral sensation, retained hardness, and remarkably increased favorability.

Example 4

Full-fat milk was homogenized (pre-heated to 60° C., 30 kgf/cm$^2$), pasteurized (75° C., 15 sec), and cooled to 31° C. to give a raw milk. 25 L of the raw milk was divided into caldrons to which a lactic acid bacterium starter (CHN-01: four-in-one mixture) (1.4% relative to the milk) was added along with 2 or 10 units of the above-mentioned purified protein deamidating enzyme product (100 units/mg) per 1 L of the raw milk, and left to stand for 1 hour. Further, to the resultant mass 0.01% $CaCl_2$ and 0.009% rennet was added, and confirmed 1 hour later to be coagulated to perform cutting (acidity 0.130, temperature 31° C. on cutting). After cutting, the resultant mass was removed of ⅓ volume whey, added with hot water with light stirring, warmed (35° C.), left to stand (approximately 20 min), and removed of another ⅓ volume whey. The resultant mass was gradually added with hot water to reach 38° C., and stirred gently at the same temperature for 1 hour.

Then, the resultant mass was squeezed in a vat at 38° C. for about 30 min, and subjected to molding and cheese curd reverse. After 30 min of preliminary squeezing (3 kg/cm$^2$), the resultant mass was reversed and substantially squeezed (5 kg/cm$^2$), then immersed into water together with the mold to cool (10° C., overnight), salted (immersed into saturated saline solution for 4 hours), dried (at 12° C. for 10 days), vacuum-packed, and matured at 12° C. to produce a hard cheese. Evaluation of the cheese was performed upon curd production and after maturation. Results of evaluation upon cheese curd production are 20 shown in Table 3, and the results of sensory test after 6 months of maturation are shown in Table 4.

As shown in Table 4, addition of protein deamidating enzyme to raw milk can provide a matured cheese with smooth oral sensation and suppressed acidic taste and bitter taste.

TABLE 3

Results of Assessment upon cheese curd production

| Amount of enzyme added (Unit/milk 1 L) | Observation of Curd texture (Cut section) | Acidic taste |
|---|---|---|
| 0 | Good | ± |
| 2 | Good | -- |
| 10 | Good | -- |

±: Control,
+: Increase,
−: Decrease

TABLE 4

Sensory Test of Cheese Curd after 6 Months of Maturation

| Amount of enzyme added (Unit/milk 1 L) | Smoothness | Hardness | Bitter taste |
|---|---|---|---|
| 0 | ± | ± | ± |
| 2 | +++ | − | -- |
| 10 | ++++ | -- | -- |

±: Control,
+: Increase,
−: Decrease

Numerous modifications and variations and variations on the present invention are possible in light of the above teachings. It is, therefore, to be understood that within the scope of the accompanying claims, the invention may be practiced otherwise than as specifically described herein.

The invention claimed is:

1. A method for manufacturing a dairy product, comprising:
   adding a protein deamidating enzyme to raw milk, wherein said raw milk comprises a milk protein; and
   maintaining said protein deamidating enzyme in contact with said milk protein in said raw milk for a time and under conditions suitable to permit said enzyme to deamidate said milk protein, wherein:
   said protein deamidating enzyme is a proteinglutaminase from chryseobacterium,
   said dairy product is selected from the group consisting of natural cheese, processed cheese, set yogurt, and stirred yogurt, and
   said protein deamidating enzyme is added to said raw milk in an amount of 0.1 to 100 units per liter of raw milk.

2. A method according to claim 1, wherein said protein deamidating enzyme is prepared from a culture liquid of a microorganism producing said protein deamidating enzyme.

3. A method according to claim 1, wherein said protein deamidating enzyme is powderized prior to said adding.

4. A method according to claim 1, wherein the activity of said protein deamidating enzyme is confirmed prior to said adding by a method comprising:
   (a) adding 10 µl of aqueous solution containing a protein deamidating enzyme to 100 µl of 176 mM phosphate buffer (pH 6.5) containing 30 mM of Z-Gln-Gly, to obtain a first mixture, reacting said first mixture at 37° C. for 10 minutes, and stopping said reacting by addition of 12% TCA solution;
   (b) adjusting the enzyme concentration to 0.05 mg/ml by an appropriate dilution with 20 mM phosphate buffer (pH 6.0), to obtain a second mixture, obtaining a supernatant liquid by subjecting said second mixture to centrifugal separation, and subjecting said supernatant liquid to quantitative measurement of $NH_3$;
   (c) adding 10 µl of said supernatant liquid and 190 µl of 0.1 M triethanolamine buffer (pH 8.0) to 100 µl of a reagent 11 liquid, to obtain a third mixture, allowing said third mixture to stand at room temperature for 5 minutes, and measuring the absorbance at 340 nm;
   (d) measuring the concentration of protein at a detection wavelength of 595 nm using a protein assay CBB (Cooumassie Brilliant Blue) solution; and
   (e) determining the activity of a protein deamidating enzyme by the following expression:

Activity (U/mg)=[(Ammonia concentration (µmol/ml) in reaction solution)×(Amount (ml) of reaction solution)×(Diluted rate of enzyme)]/[(Amount (ml) of enzyme solution)×(Concentration (mg/ml) of protein)×(Reaction time (min))].

5. A method according to claim 1, wherein said raw milk is an edible milk selected from the group consisting of cow milk, buffalo milk, goat milk, sheep milk, and horse milk.

6. A method according to claim 1, wherein said raw milk is in a form selected from the group consisting of a pasteurized milk, a milk formulated in milk fat, a diluted milk, a concentrated milk, a dried milk, a defatted dry milk, a defatted milk solution, and a processed milk.

7. A method according to claim 1, wherein said dairy product is a cheese.

8. A method according to claim 1, wherein said dairy product is a yogurt.

9. A method according to claim 1, wherein said maintaining is carried out at a temperature of from 5 to 80° C.

10. A method according to claim 1, wherein said maintaining is carried out at a temperature of from 20 to 60° C.

11. A method according to claim 1, wherein said maintaining is carried out at a pH of from 2 to 10.

12. A method according to claim 1, wherein said maintaining is carried out at a pH of from 4 to 8.

13. A method according to claim 1, wherein said maintaining is carried out for a time ranging from 10 seconds to 48 hours.

14. A method according to claim 1, wherein said maintaining is carried out for a time ranging from 10 minutes to 24 hours.

15. A method according to claim 1, wherein said protein deamidating enzyme is encoded by a polynucleotide having the sequence of SEQ ID NO: 1.

16. A method according to claim 1, wherein said protein deamidating enzyme has the amino acid sequence of SEQ ID NO: 2.

17. A method according to claim 1, wherein said protein deamidating enzyme corresponds to the mature peptide fragment of the amino acid sequence of SEQ ID NO: 2.

* * * * *